CHRYSANTHEMUM PLANT

Filed Sept. 23, 1970 2 Sheets-Sheet 1

INVENTORS
WALTER H. JESSEL, JR.,
WILLIAM E. DUFFETT
BY
Oberlin, Maky, Donnelly & Renner
ATTORNEYS INVENTORS
WALTER H. JESSEL, JR.,
WILLIAM E. DUFFETT
BY
Oberlin, Maky, Donnelly & Renner
ATTORNEYS

United States Patent Office

Plant Pat. 3,191
Patented May 23, 1972

3,191

CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 23, 1970, Ser. No. 74,943
Int. Cl. A01h *5/00*
U.S. Cl. Plt.—78 1 Claim

The present invention comprises a new and distinct variety of chrysanthemum plant which is a seedling of #61427–1 × #6251–1. Both of these parents are unnamed and unpatented, and are identified by such number for breeding purposes by Yoder Brothers, Inc., Barberton, Ohio, the assignee of the present invention.

The new variety is similar in many respects to Southern Sun, an unpatented but well-known commercial variety of Yoder Brothers, Inc., Barberton, Ohio, assignee of the present invention. The new variety has the same characteristics as Southern Sun of:

(1) Early 9 week response.
(2) Very uniform response.
(3) Resistance to sun scald.

The new variety is distinguished from Southern Sun by the following characteristics:

(1) Shorter in vigor by approximately 9"–14".
(2) A deeper yellow color.
(3) A more tightly incurved form, with high crown.
(4) Longer form retention.
(5) A heavier stem.
(6) A ½"–1" smaller flower.
(7) A very uniform size and grade.
(8) Superior tolerance to high temperatures.

Our new variety has been asexually reproduced by cuttings at Barberton, Ohio, and has been found to retain its distinctive characteristics through successive propagations.

The new variety, when grown in the vicinity of Barberton, Ohio, has a response period of approximately 9 weeks, and the following detailed description is based on observations made of the new variety in a greenhouse in Barberton, Ohio. The response time and blooming period may vary significantly with varying and environmental conditions such as temperature, light intensity, and day length. Suggested flowering in the northern and central United States is May through October. In coastal California, from April to mid-November; and for southern Florida, from December through April.

Figure 1:
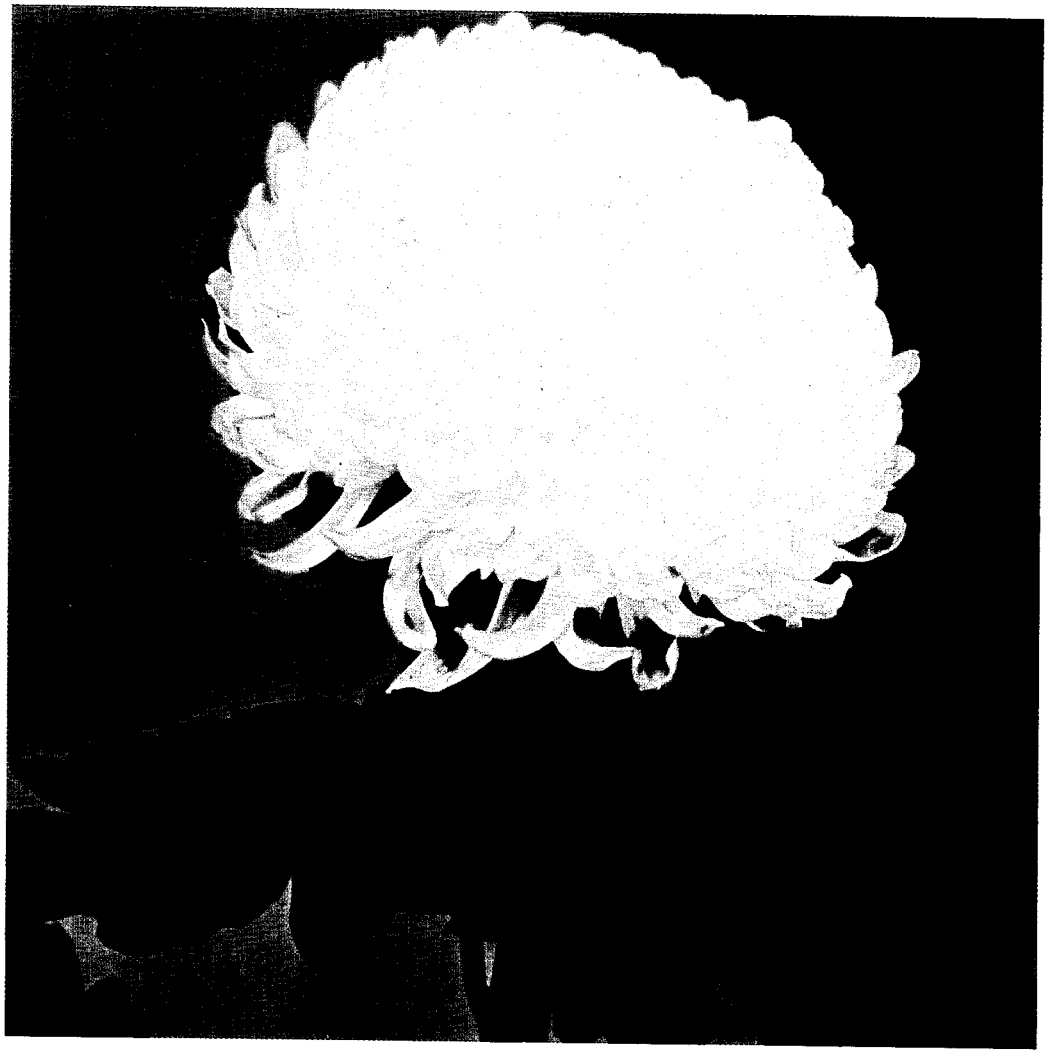
Figure 2:
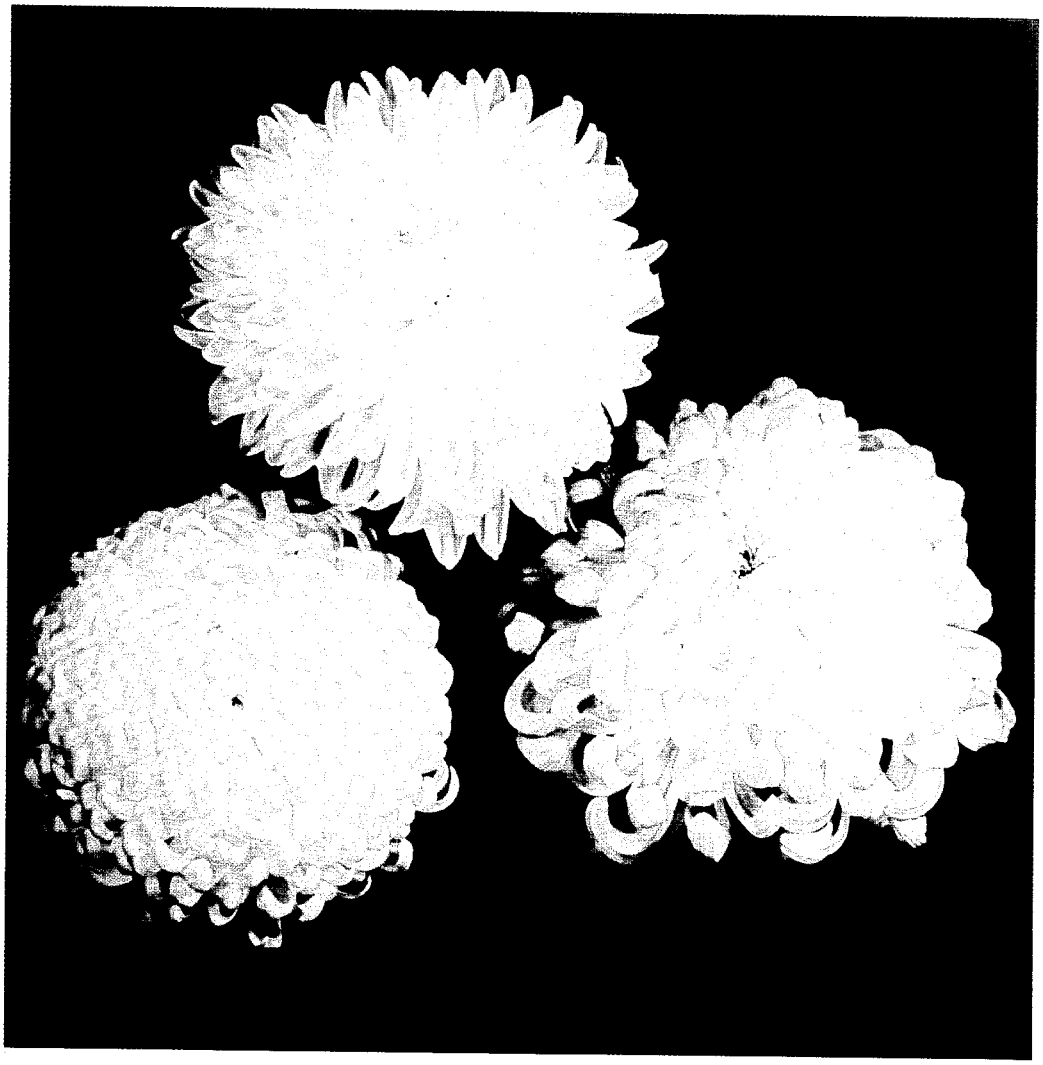

The accompanying drawings show the unique characteristics of our new variety, the colors being as nearly true as possible with color illustrations of this type. FIG. 1 is of the new variety itself and FIG. 2 is a comparison view wherein the new variety is shown in the lower left, the variety Southern Sun on top, and the variety Golden Nob Hill on the lower right. This latter variety is also a well-known commercial variety of Yoder Brothers, Inc.

The following data is based on observations made of the new variety in a greenhouse in Barberton, Ohio. Color references are to the Munsell Color Book, 1963 edition, and comparisons have been made in certain instances with the cultivar Southern Sun.

Botanical classification: *Chrysanthemum morifolium.*

| | Morocco | Southern Sun |
|---|---|---|
| Bloom: | | |
| Size | 4¾"–5" | 5"–5½". |
| Fully expanded | 5"–5¾" | 5½"–6½". |
| Borne | Single on a disbudded plant. | Single on a disbudded plant. |
| Stems | Wiry | Wiry. |
| Form | Incurved | Semi-incurved. |
| Permanence | 8–10 days | 8–10 days. |
| Color (Munsell): | | |
| Center of flower. | Golden ellow, 6.25Y8.5/12. | Light ellow, 7.5Y-8.50/6. |
| Base of petals | do | Do. |
| Inside of petals | do | Do. |
| Reverse of petals. | Golden yellow, 5Y8.5/8. | Do. |
| Tonality from a distance. | Golden yellow | Lemon yellow. |
| Discoloration | Golden yellow, 7.5Y8.5/12. | Light yellow, 7.5Y8.50/6. |

Petals:

*Texture.*—Smooth.

*Appearance.*—Deeply keeled at base; narrow with a blunt point.

*Arrangement.*—Composite, whorled on a single receptacle.

*Persistence.*—Resist shatter.

*Fragrance.*—Typical chrysanthemum.

Reproductive organs:

*Stamens, anthers.*—0 to 15.

*Pollen.*—Very scant.

*Arrangement.*—Clustered in center of flower, if present.

*Styles.*—Present in both ray and disc floret.

*Length.*—Short.

*Ovaries.*—At base of petals attached to receptacle.

Plant:

*Form.*—Herbaceous.

*Growth.*—Upright.

*Height.*—37" to 40" depending on culture.

*Spread*—None with single stem culture; slight with pinched crops.

| | Morocco | Southern Sun |
|---|---|---|
| Foliage: | | |
| Top side | Dull cast dark green, 7.5GY2/4. | Shiny cast dark green, 7.5GY2/4. |
| Size | 7"–8" long, 3¾"/4"–4¼" wide. | 5½" long, 3½" wide. |
| Quantity | Numerous | Numerous. |
| Shape | Spatulate lobed | Spatulate lobed. |
| Texture | Coarse | Coarse. |
| Ribs and veins | Very prominent | Prominent. |
| Edge | Moderately indented | Indented. |
| Serration | Slight | Moderate. |
| Underside | Light green, 7.5GY5/4 | Light green, 7.5GY4/4. |
| Stipules | Present | Present. |

In FIG. 2, it will be noted that the new variety is more lightly incurved in form than Golden Nob Hill. Although not visible from the illustration, the new variety further distinguishes itself from Golden Nob Hill by its earlier response, superior uniform grade, high temperature tolerance and better form retention.

We claim:

1. A new and distinct variety of chrysanthemum characterized particularly as to uniqueness by a strong rigid stem habit, superior uniformity of growth and response, tightly incurved form, superior form retention, uniform size and grade, resistance to high temperatures, and an intense golden yellow color.

No references cited.

ROBERT E. BAGWILL, Primary Examiner

UNITED STATES PATENT OFFICE
CERTIFICATE OF CORRECTION

Patent No. PP-3,191 Dated May 23, 1972

Inventor(s) WALTER H. JESSEL, JR. and WILLIAM E. DUFFETT

It is certified that error appears in the above-identified patent and that said Letters Patent are hereby corrected as shown below:

In column 2, line 7, adjacent the heading "Fully expanded" and under the cultivar "Morocco" change "5-3/ " to --5-3/4--.

In column 2, line 13, in the description of "Center of flower", add the "y" to yellow under both "Morocco" and "Southern Sun".

In column 2, line 15, in the description under "Reverse of petals", under "Southern Sun", the description should be --Light yellow, 7.5Y9/4--.

In column 2, line 54, in the description under "Size" under "Morocco", "7" - 8" long, 3-3/4"/4" - 4-1/4" wide" should be --7" - 8" long, 3-3/4" - 4-1/4" wide--.

Signed and sealed this 25th day of September 1973.

(SEAL)
Attest:

EDWARD M.FLETCHER, JR.
Attesting Officer

RENE D. TEGTMEYER
Acting Commissioner of Patents